US011950800B2

(12) United States Patent
Chanduszko et al.

(10) Patent No.: US 11,950,800 B2
(45) Date of Patent: *Apr. 9, 2024

(54) CATHETER WITH GUIDED, TRANSLATABLE CUTTER FOR ACTIVE SLICING/SCORING AND RELATED METHODS

(71) Applicant: C.R. BARD, INC., Tempe, AZ (US)

(72) Inventors: Andrzej Chanduszko, Chandler, AZ (US); Michael Randall, Gilbert, AZ (US); Chad Van Liere, Phoenix, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/351,464

(22) Filed: Jun. 18, 2021

(65) Prior Publication Data

US 2021/0315606 A1 Oct. 14, 2021

Related U.S. Application Data

(63) Continuation of application No. 16/472,075, filed as application No. PCT/US2018/045375 on Aug. 6, 2018, now Pat. No. 11,039,853.

(51) Int. Cl.
*A61B 17/3207* (2006.01)
*A61B 17/22* (2006.01)
(Continued)

(52) U.S. Cl.
CPC ... *A61B 17/320725* (2013.01); *A61M 25/104* (2013.01); *A61B 2017/22051* (2013.01);
(Continued)

(58) Field of Classification Search
CPC ...... A61B 17/32075; A61B 17/320725; A61B 17/3207; A61B 2017/22051; A61M 25/104; A61M 2025/109

See application file for complete search history.

(56) References Cited

U.S. PATENT DOCUMENTS 5,192,295 A * 3/1993 Danforth ............. A61M 25/104
600/585
7,029,450 B2 * 4/2006 Gellman ............... A61M 25/10
600/549

(Continued)

FOREIGN PATENT DOCUMENTS

CN 103654912 A 3/2014
JP 2012081267 A 4/2012
JP 2016520369 A 7/2016

*Primary Examiner* — Ashley L Fishback
(74) *Attorney, Agent, or Firm* — Dickinson Wright PLLC; Andrew D. Dorisio

(57) ABSTRACT

A catheter for scoring or slicing a lesion. The catheter has a first receiver at a distal end of an expandable portion of the catheter shaft. A first carrier at least partially within the first receiver is moveable axially along the catheter shaft to deploy a first cutter along the expandable portion for cutting or scoring the lesion. In an alternative embodiment, the first carrier may be a wire having a loop, and thus forming a first length including the first cutter and a second length including a second cutter. Actuation of the wire thus causes simultaneous, reciprocal movement of the first and second cutters. Related methods are also disclosed.

20 Claims, 11 Drawing Sheets

(51) Int. Cl.
A61B 90/00 (2016.01)
A61M 25/10 (2013.01)

(52) U.S. Cl.
CPC ............... *A61B 2090/3966* (2016.02); *A61M 2025/1079* (2013.01); *A61M 2025/109* (2013.01)

(56) References Cited

U.S. PATENT DOCUMENTS

| | | | |
|---|---|---|---|
| 7,901,378 B2* | 3/2011 | Solar | A61K 31/47 604/164.13 |
| 8,052,701 B1* | 11/2011 | Cox | A61B 17/32075 623/1.14 |
| 10,327,802 B2* | 6/2019 | Schur | A61B 17/320725 |
| 2004/0193196 A1* | 9/2004 | Appling | A61B 17/320725 606/167 |
| 2014/0324079 A1 | 10/2014 | Silvestro | |
| 2016/0317174 A1* | 11/2016 | Dake | A61B 17/320016 |
| 2017/0100570 A1* | 4/2017 | Giasolli | B29C 65/48 |
| 2020/0155815 A1* | 5/2020 | Giasolli | A61M 25/1029 |

\* cited by examiner

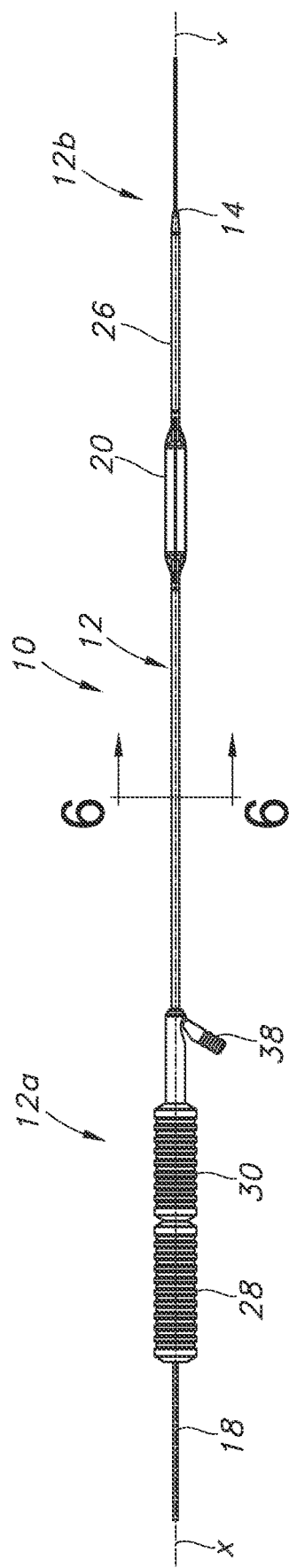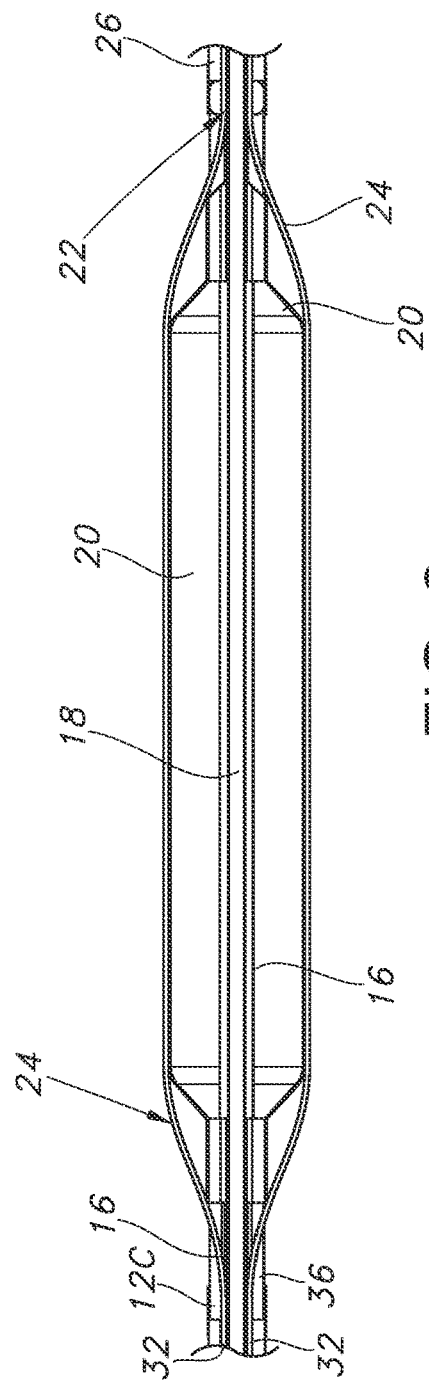

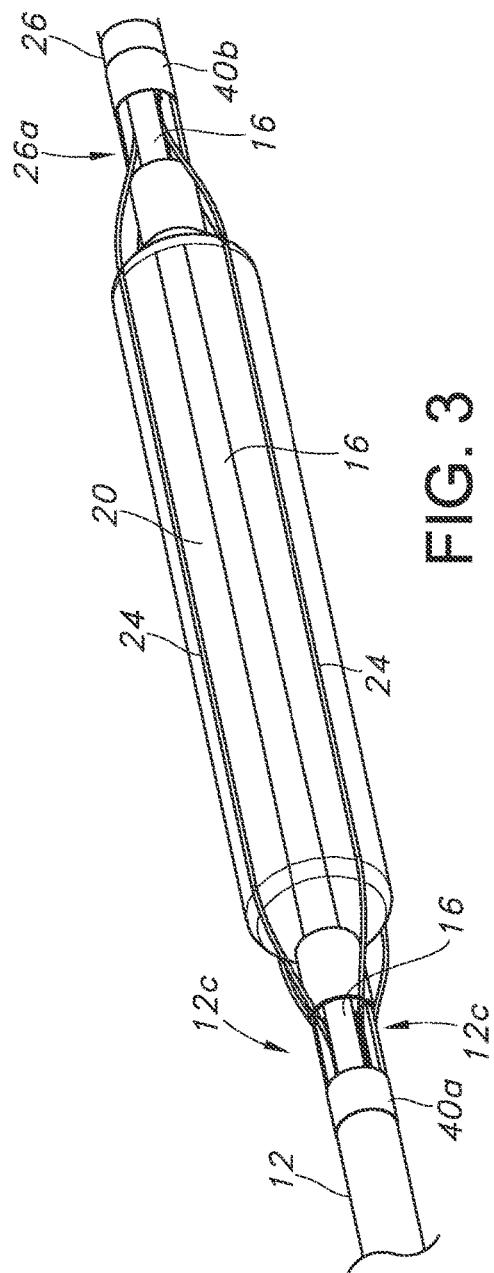
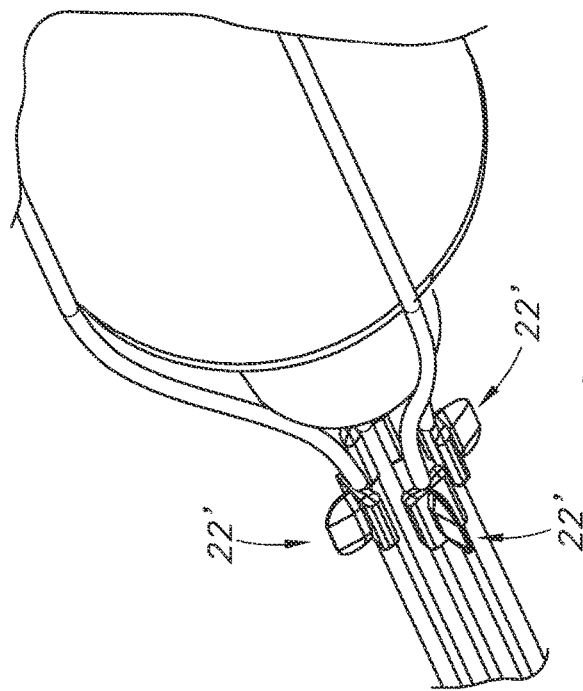
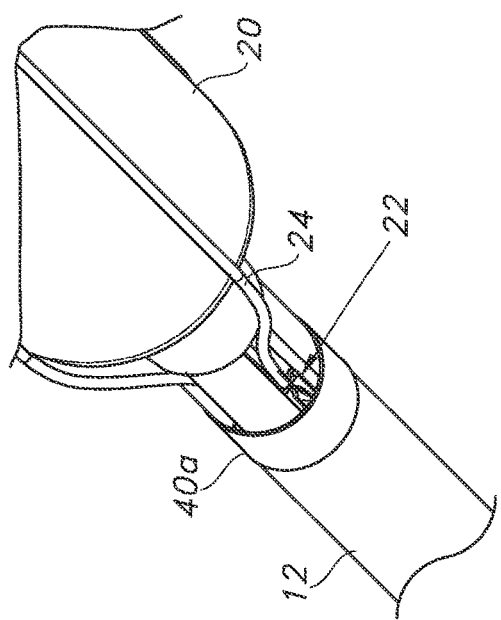

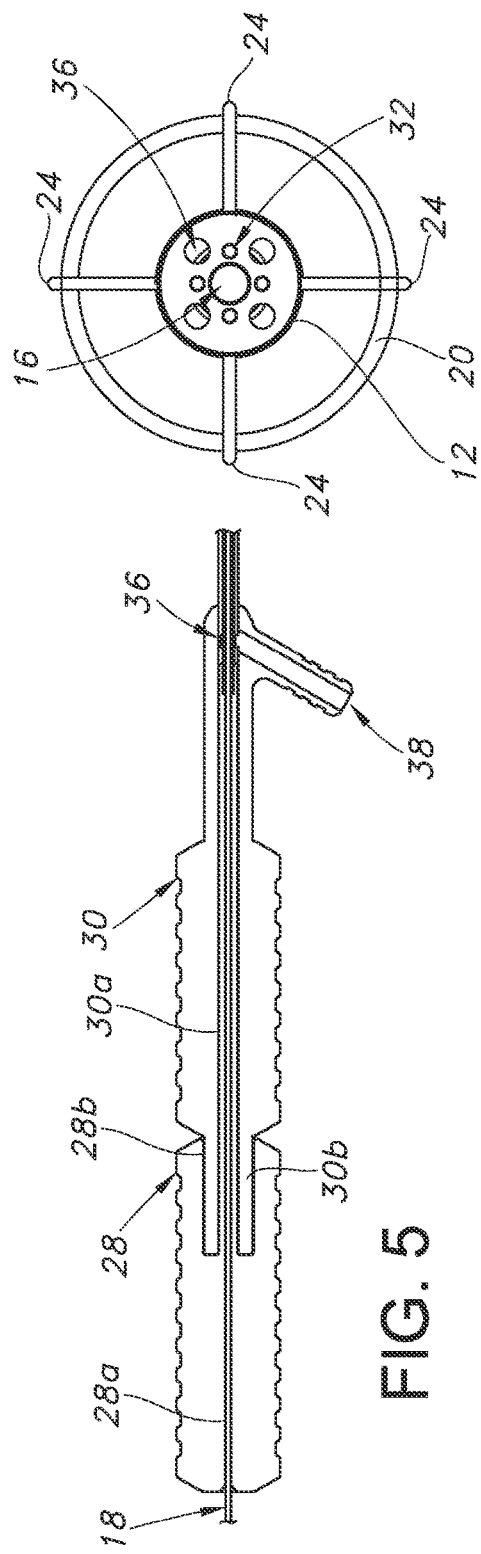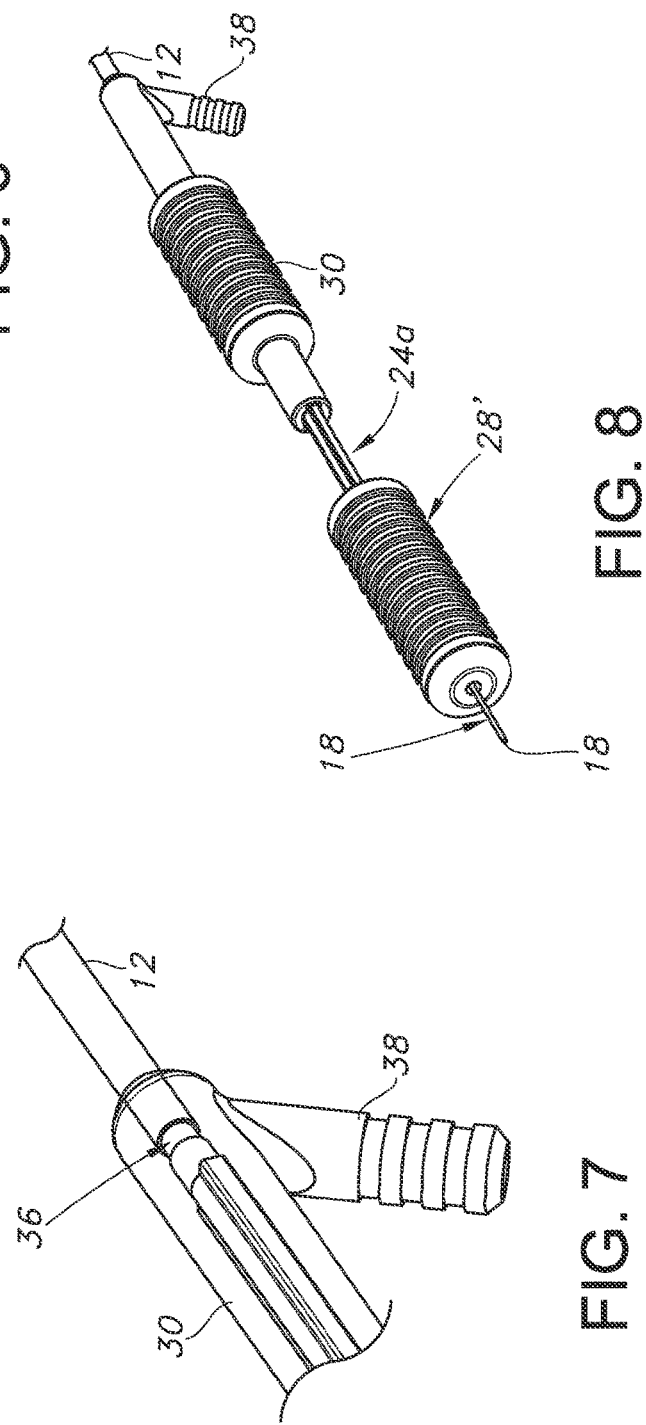
FIG. 5
FIG. 6
FIG. 7
FIG. 8

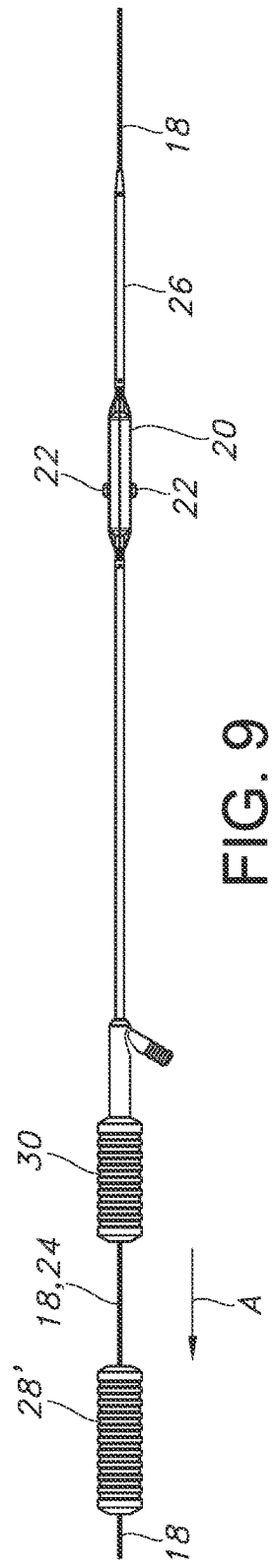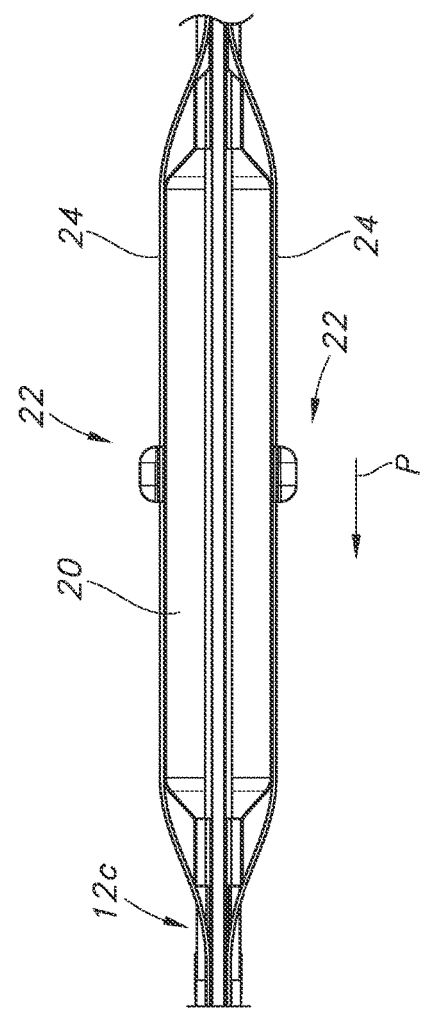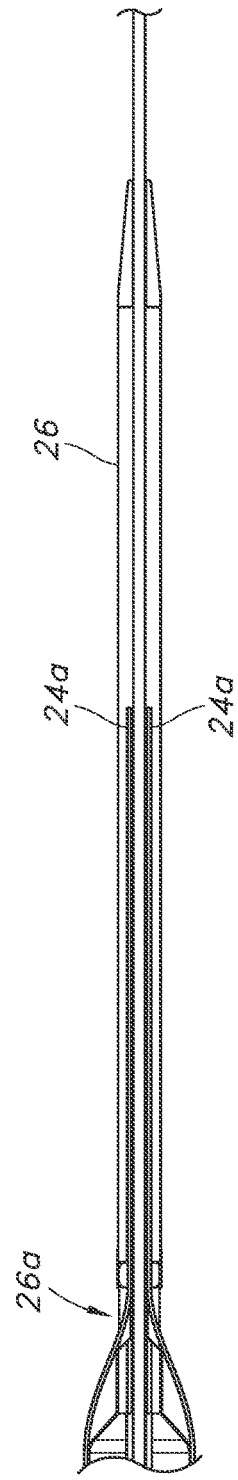
FIG. 9
FIG. 10
FIG. 11

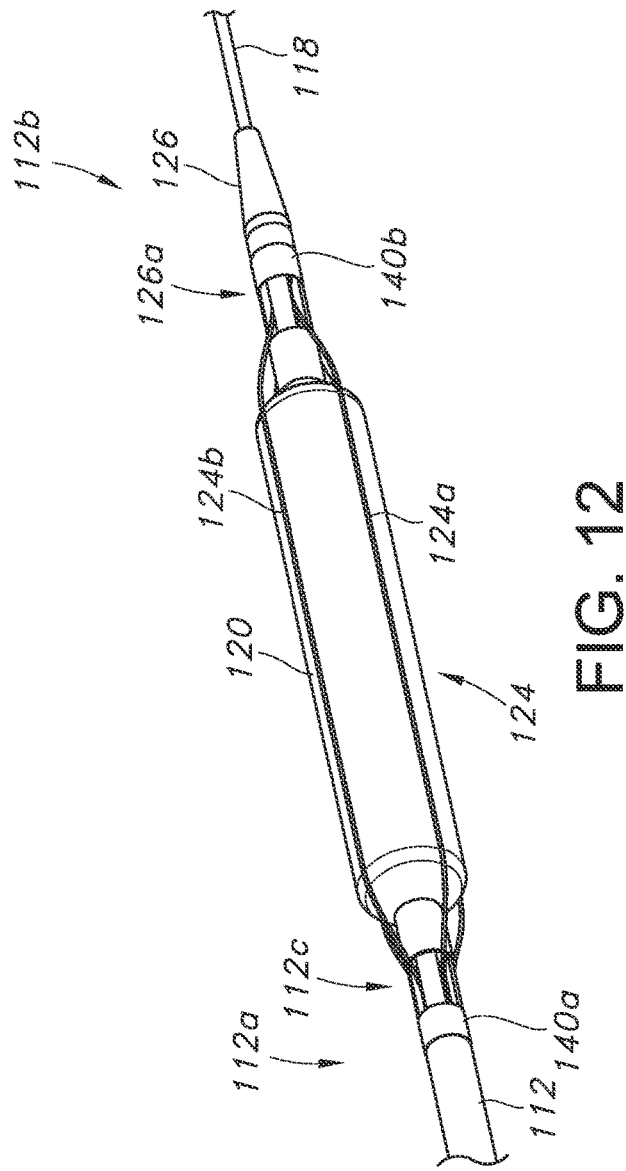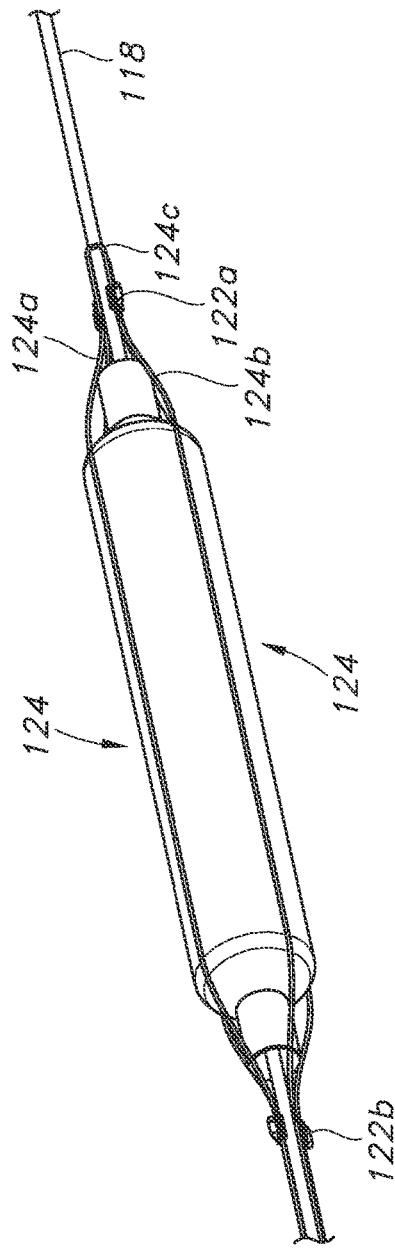

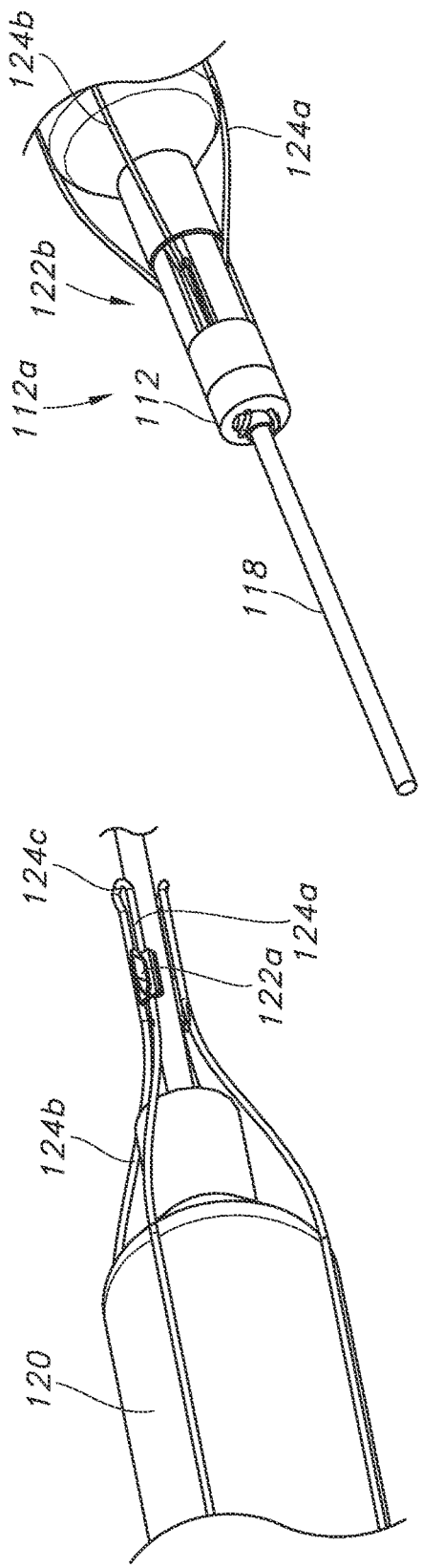
FIG. 14
FIG. 15
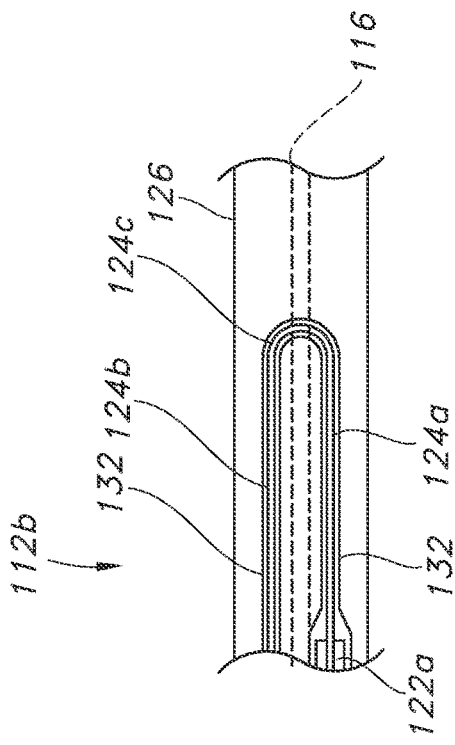
FIG. 16

CATHETER WITH GUIDED, TRANSLATABLE CUTTER FOR ACTIVE SLICING/SCORING AND RELATED METHODS

INCORPORATION BY REFERENCE

This application is a continuation of U.S. Ser. No. 16/472,075 filed on Jun. 20, 2019, which is a National Stage of PCT/US2018/045375 filed on Aug. 6, 2018, the disclosures of which are incorporated herein by reference.

All publications and patent applications mentioned in this specification are herein incorporated by reference to the same extent as if each individual publication or patent application was specifically and individually indicated to be incorporated by reference.

TECHNICAL FIELD

This disclosure pertains to devices for providing endovascular treatment and, in particular, a catheter with one or more guided, translatable cutters for actively slicing or scoring a lesion or like obstruction in the vasculature.

BACKGROUND

Balloon dilatation catheters are used to treat lesions in vessels, such as by way of angioplasty. While successful for use in a variety of applications or locations in the vasculature, some situations call for a different approach in view of the possibility of "elastic recoil," which refers to the inherent resistance of a tissue to changes in shape, and the tendency of the tissue to revert to its original shape once deformed. Furthermore, some applications, and particularly those "below the knee" (BTK) involve hard calcifications, for which balloon angioplasty alone may be contraindicated. Moreover, the use of pharmacological agents to lesions for enhanced treatment may be desirable in some instances, and efficacy may be increased by actively scoring or slicing prior to application.

A desire also exists for active slicing or scoring of lesions. In this regard, others have proposed a scoring element connected to a wire that may be moved to and fro relative to a balloon prior to being expanded (see, e.g., U.S. Patent Application Publication No. 2016/0249942). However, this proposal fails to provide active guidance for the scoring element, which is free to move laterally along the balloon and thus may not be useful for slicing or scoring a lesion. It is also complicated by the requirement for multiple catheter tubes: one for the balloon, and another for the scoring element(s), which leads to added cost and complexity.

Accordingly, it would be desirable to provide a simple, yet effecting slicing or scoring catheter for treating lesions. Such a catheter would be readily useful in a variety of locations in the vasculature, including where particularly hard calcifications might be present, and conditions dictate a more reliable and effective approach than known proposals for slicing/scoring catheters.

SUMMARY

An object of the invention is to provide a catheter for actively slicing/scoring a plaque, lesion, or other obstruction that addresses and overcomes the foregoing limitations, and possibly others that have yet to be discovered.

According to one aspect of the disclosure, a catheter for scoring or slicing a lesion in a vessel is provided. The catheter includes a catheter shaft including a first receiver adjacent a distal end of an expandable portion of the catheter shaft. A first carrier is positioned at least partially within the first receiver and moveable axially to deploy a first cutter along the expandable portion (which may be axially aligned with the catheter or offset from a longitudinal axis thereof in all embodiments) for cutting or scoring the lesion.

In one embodiment, a first radiopaque marker is provided distal of the expandable portion for marking a distal non-deployed position of the first cutter. The catheter may further include a second receiver proximal of the expandable portion for receiving the first cutter in a proximal non-deployed position. A second radiopaque marker proximal of the expandable portion may also be provided for marking a non-deployed proximal position of the first cutter.

In one embodiment, the first carrier includes a loop distal of the expandable portion, and a second cutter is provided proximal to the expandable portion for moving distally along the expandable portion when the first cutter is moved to a deployed position. A second receiver may be provided proximal of the expandable portion for receiving the second cutter in a non-deployed proximal position.

In another embodiment, a second carrier is at least partially received by the first receiver, the second carrier moveable axially along the catheter shaft to deploy a second cutter attached to the second carrier along the expandable portion for cutting or scoring the lesion. A second receiver may be provided proximal of the expandable portion for receiving the first cutter in a proximal non-deployed position. The catheter may further include a pull at a proximal end of the catheter shaft connected to the first carrier and the second carrier.

In yet another embodiment, a plurality of second carriers are provided at least partially within the first receiver. Each of the plurality of second carriers is moveable axially along the catheter shaft. This movement serves to deploy a second cutter attached to each of the second carriers along the expandable portion for cutting or scoring the lesion. A second receiver may be provided proximal of the expandable portion for receiving each of the second cutters in a proximal non-deployed position, along with a pull at a proximal end of the catheter shaft connected to the first carrier and the plurality of second carriers.

The expandable portion may comprise an inflatable balloon supported by the shaft. In such case, the shaft may further include an inflation lumen for supplying fluid to the inflatable balloon. The expandable portion may comprise an expandable frame, such as made of one or more wires.

The first receiver may comprise a sheath connected to the catheter shaft for receiving and at least partially covering a portion of the first carrier including the first cutter. The catheter shaft and sheath may each include a guidewire lumen. In any of the foregoing embodiments, the first carrier may comprise a wire.

According to a further aspect of the disclosure, a catheter for scoring or slicing a lesion in a vessel comprises a catheter shaft having an expandable portion and a first carrier extending along the expandable portion. The first carrier includes a first cutter adjacent a proximal end of the expandable portion and a second cutter adjacent to a distal end of the expandable portion. The first carrier is adapted for moving the first cutter along the expandable portion toward the distal end while moving the second cutter along the expandable portion toward the proximal end.

The first carrier may comprise a wire having a loop. The loop may be distal of the expandable portion. A first receiver may be provided for receiving the first cutter at a proximal end of the expandable portion and a second receiver may be provided for receiving the second cutter at a distal end of the expandable portion. A first radiopaque marker may be provided proximal of the expandable portion for marking a non-deployed proximal position of the first cutter and a second radiopaque marker may be provided distal of the expandable portion for making a non-deployed distal portion of the second cutter.

According to a further aspect of the disclosure, a catheter for scoring or slicing a lesion in a vessel comprises a catheter shaft including a first receiver at a distal end of an expandable portion of the catheter shaft. A first cutter lies at least partially within the first receiver. The first cutter is moveable axially along the catheter shaft to a deployed position along the expandable portion for cutting or scoring the lesion.

In one embodiment, the catheter further includes a carrier connected to the first cutter. The carrier may comprise a wire having a first portion received within a second receiver proximal of the expandable portion of the catheter shaft and a second portion received within the first receiver. The wire may have a loop forming a first length attached to the first cutter and a second length attached to a second cutter. The catheter shaft may include a second receiver proximal of the expandable portion for receiving the second cutter in a non-deployed condition.

Still a further aspect of the disclosure relates to a method of scoring or slicing a lesion in a vessel. The method comprises providing a catheter shaft, including an expandable portion and a carrier including a first cutter. While the expandable portion is expanded, the method further comprises moving the carrier axially along a longitudinal axis of the catheter shaft between a first position wherein the first cutter does not perform a cutting or scoring function and a second position wherein the first cutter performs a cutting or scoring function.

In one version of the method, the moving step comprises pulling the carrier connected to the first cutter. The carrier may comprise a wire, and the step of moving the carrier axially may comprise pulling a first portion of the wire proximally while a second portion of the wire including a second cutter is moved distally. The catheter may include a plurality of carriers, each including at least one cutter, and the moving step comprises moving each wire simultaneously. The moving of one or more of the cutters may comprise pulling the catheter proximally with the cutter(s) in a deployed position.

Yet a further aspect of the disclosure relates to a method of scoring or slicing a lesion in a vessel. The method comprises slicing or scoring the lesion by moving a plurality of cutters in a reciprocal manner along an expanded portion of a catheter. The plurality of cutters may be connected to a wire, and the step of slicing or scoring the lesion may comprise pulling a first portion of the wire proximally while a second portion of the wire including a second cutter moves distally. The method may include the step of moving the catheter proximally with the cutters is a deployed position.

BRIEF DESCRIPTION OF THE DRAWING FIGURES

The above and further advantages of the invention according to the disclosure may be better understood by referring to the following description in conjunction with the accompanying drawings in which:

FIG. 1 is a side view of a catheter for actively scoring or slicing a lesion;

FIG. 2 is an enlarged, cutaway side view of an expandable portion of the catheter;

FIG. 3 is an enlarged, cutaway perspective view of an expandable portion of the catheter;

FIGS. 3A and 3B are cutaway bottom views of portions of a proximal end of the scoring or slicing catheter of FIG. 1, with the cutters in a non-deployed proximal position;

FIG. 5 is a cutaway side view of a proximal end of the catheter;

FIG. 6 is a cross-sectional view along line 6-6 of FIG. 1;

FIG. 7 is a cutaway perspective view of a portion of the proximal end of the catheter of FIG. 1;

FIG. 8 is another cutaway perspective view of a portion of the proximal end of the catheter of FIG. 1;

Figure 17:
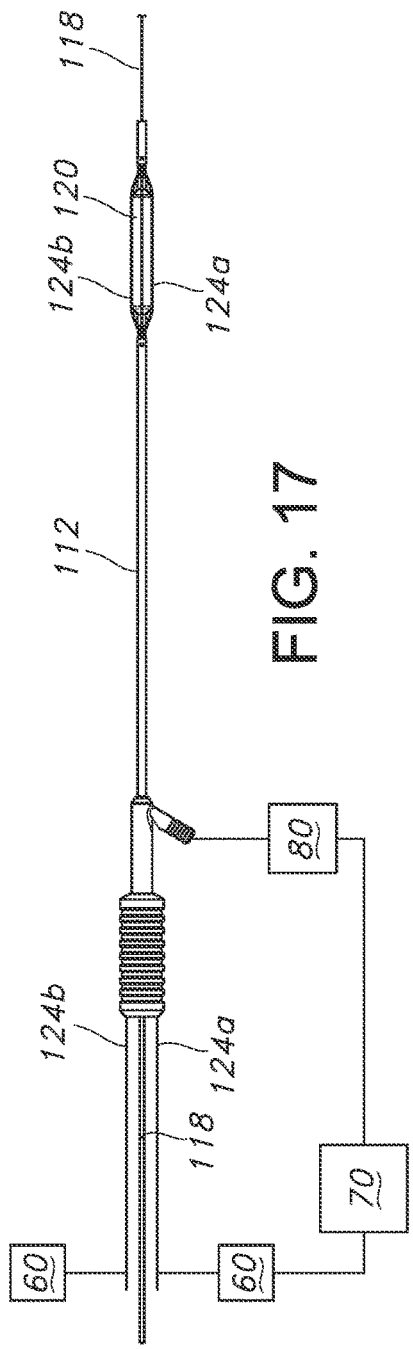
Figure 18:
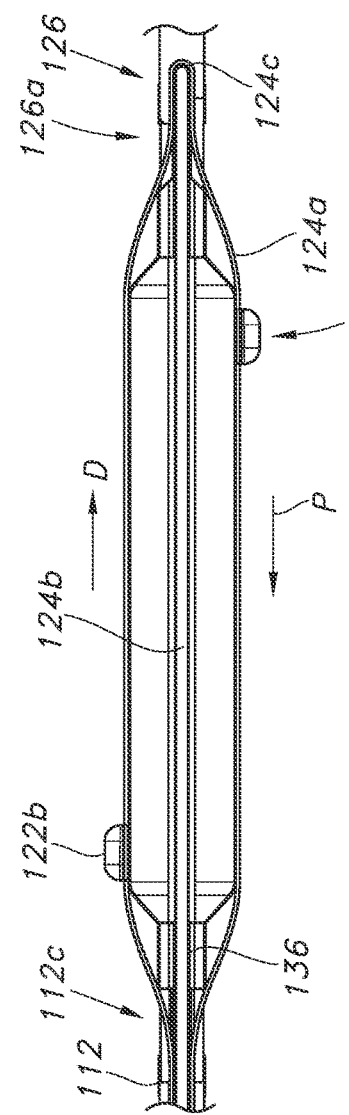
Figure 19:
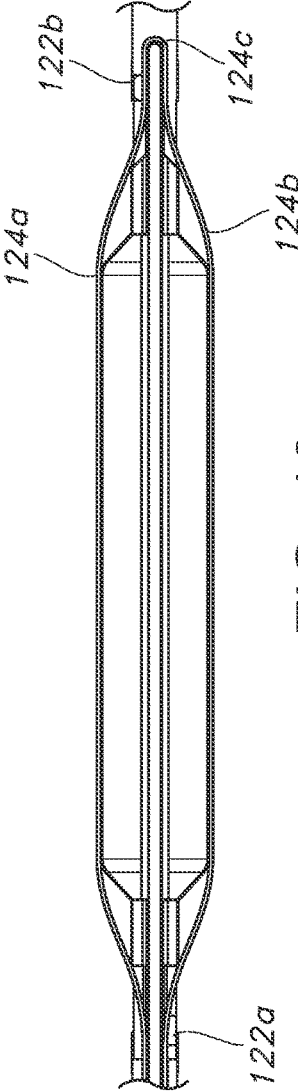
Figure 20:
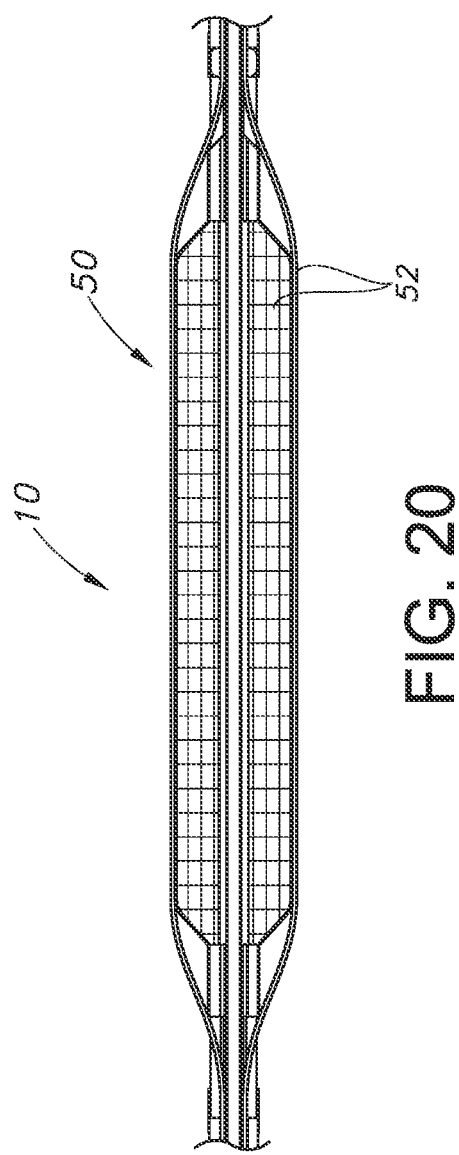
Figure 21:
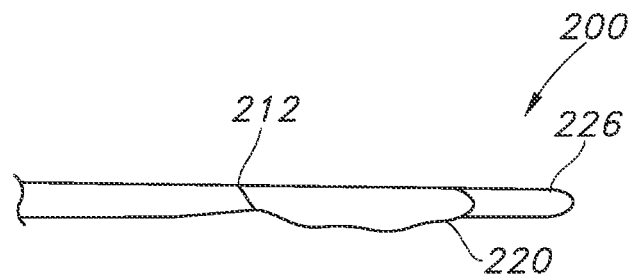
Figure 22:
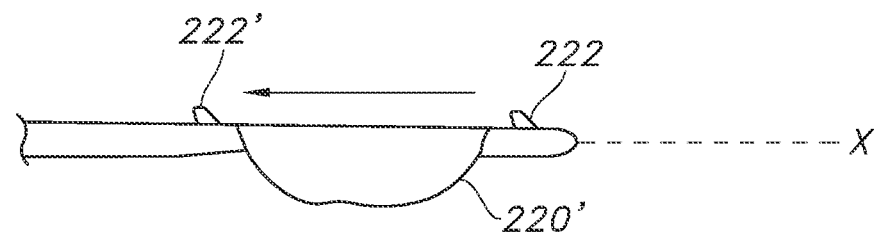
Figure 23:
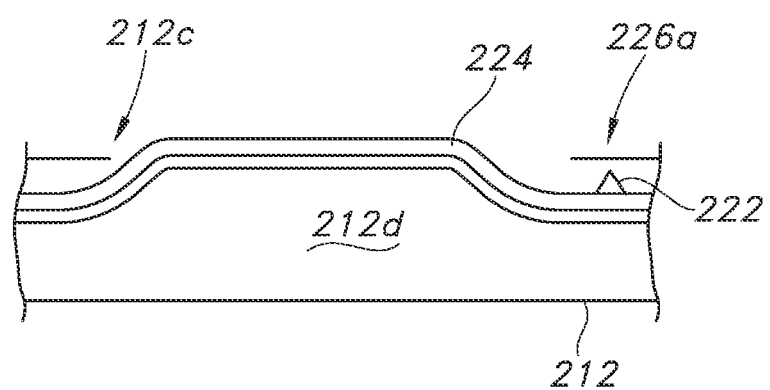

FIGS. 9, 10, and 11 are full side and cutaway views showing one possible actuation sequence for the active slicing or scoring catheter;

FIGS. 12 and 13 are perspective cutaway views of a second embodiment of an active scoring or slicing catheter;

FIGS. 14 and 15 are cutaway perspective views of the embodiment of FIGS. 12 and 13;

FIG. 16 is a cross-sectional view of a portion of the catheter of the second embodiment;

FIGS. 17, 18, and 19 are full side and cutaway views showing one possible actuation sequence for the active slicing or scoring catheter of FIGS. 12 and 13;

FIG. 20 is an alternate embodiment of a catheter including an expandable portion in the form of a wire frame;

FIGS. 21-23 relate to a further alternate embodiment of a catheter including an expandable portion.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Referring first to FIGS. 1 and 2, a first embodiment of a slicing/scoring catheter 10 according to the disclosure is illustrated. The catheter 10 includes an elongated body or shaft 12 having a proximal end 12a and a distal end 12b, which may include a tip 14. While elongated along a longitudinal axis X and in a corresponding longitudinal direction, the shaft 12 is illustrated in a compact form simply for ease of illustration, and would normally have a considerable length (e.g., 100-200 centimeters, or otherwise suitable to allow the distal end 12b to reach a treatment area of interest in the vasculature while the proximal end 12a remains accessible external to the vasculature). As perhaps best understood from FIG. 2, the shaft 12 may also include a lumen 16 for receiving a guidewire 18, which may be used to guide the catheter 10 to a location in the vasculature for providing a treatment.

In order to provide a slicing or cutting function in an effective and reliable manner, and with added reference to FIGS. 3 and 3A-3D, the catheter 10 may include a portion that may be selectively expanded once located at or adjacent to an area in need of treatment. In the illustrated embodiment, this expandable portion comprises an inflatable balloon 20 associated with one or more selectively deployable cutters 22 associated with a carrier, such as a wire 24. While only one cutter 22/wire 24 combination may be provided in a simple form of the invention, a plurality (four) are provided in the illustrated embodiment (see FIG. 5). Consequently, cutting or scoring of a lesion may occur on all sides of the catheter 10. Also, while only one cutter 22 is shown on each carrier (wire 24) more than one may be provided (such as spaced along the longitudinal axis X).

Figure 3D:
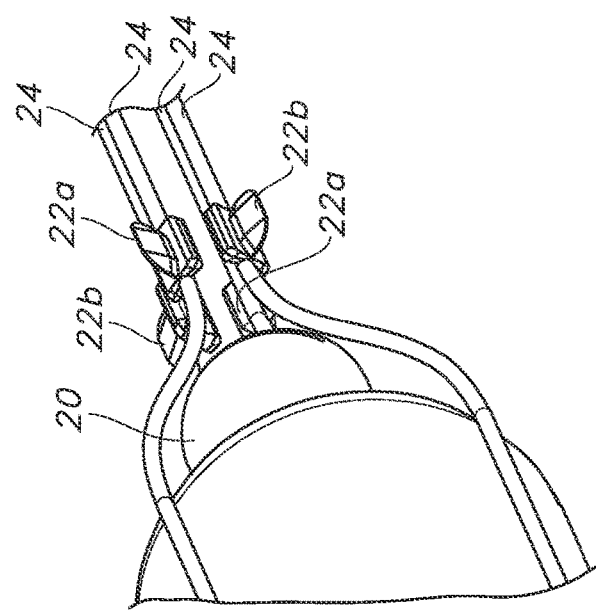
FIGS. 3C and 3D are cutaway bottom views of portions of a proximal end of the scoring or slicing catheter of FIG. 1, with the cutters in a non-deployed distal position.

With continued reference to FIGS. 3B and 3D, it can be understood that each cutter 22 includes an upstanding blade 22a connected to a base 22b. The base 22b is in turn attached to the carrier, such as wire 24 (such as by welding, interference fit, etc.), adapted to translate to and fro along the longitudinal axis X along a portion of the shaft 12. This includes moving over and along the expandable portion in an expanded condition (which, in the case of balloon 20, may be selectively caused by an inflation fluid, as described further below) to score or slice an adjacent or surrounding lesion due to the increased diameter provided. FIG. 3D shows the cutters 22 in a nominal, non-deployed position at the distal end of the expandable portion (balloon 20), whereas, FIG. 3B shows the same cutters 22' once translated to a non-deployed proximal position, such as after performing a scoring or slicing function.

In any case, the carriers or wires 24 may pass along and partly through the catheter 10 from the proximal end 12a to the distal end 12b of the shaft 12. This movement provides the desired relative translating movement to deploy the attached cutters 22 for scoring or slicing a lesion when the expandable portion or balloon 20 is expanded. As perhaps best understood from FIGS. 3 and 3A-3D, the catheter shaft 12 includes a receiver for receiving a distal portion of each wire 24 and the associated cutter 22 proximal thereof in a non-deployed position, distal of the expandable portion (balloon 20). As indicated in FIG. 3C, this receiver may comprise a sheath 26 forming part of the shaft 12 distal of the expandable portion, or balloon 20, which sheath serves to receive and cover a distal end 24b of each wire 24 and the associated cutter 22 in a non-deployed condition.

Figure 3C:
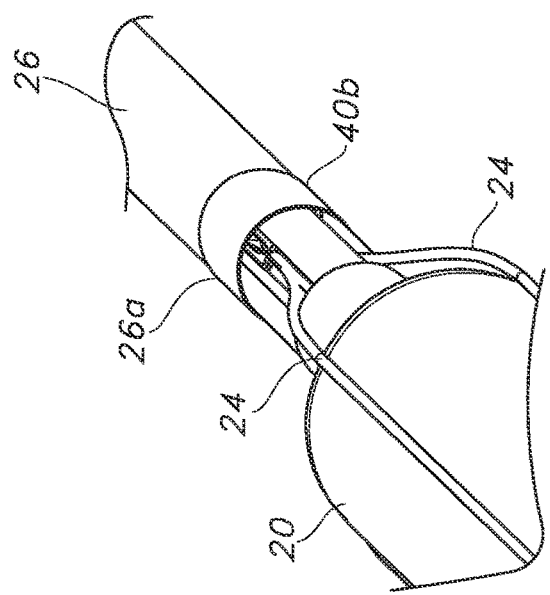
Figure 4:
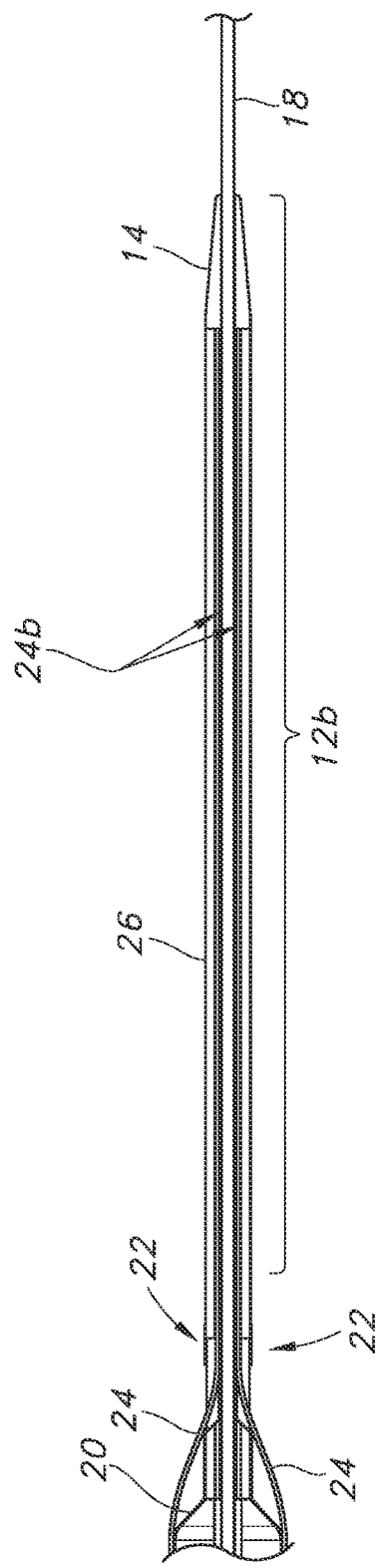
FIG. 4 is a cutaway side view of a distal portion of the catheter of FIG. 1.

As perhaps best understood from FIGS. 3C and 4, a proximal portion of the sheath 26 adjacent to the expandable portion (balloon 20) may have open-ended passages 26a for receiving the cutters 22 in a non-deployed distal position and the distal ends 24b of the wires 24 (which distal ends are distal of the cutters 22, and thus remain enclosed by the sheath 26 during deployment to provide a guiding function for the cutter(s)). Similar open-ended passages 12c may be provided in the shaft 12 adjacent the proximal end of the balloon 20, as indicated in FIGS. 3 and 3A. These passages 12c, 26a on opposite ends of the balloon 20 serve as the receivers for allowing the proximal ends 24a of the wires 24 to pass into the shaft 12, and also for receiving the associated cutter 22 once drawn to a non-deployed position at the proximal end of the expandable portion or balloon 20.

Figure 5A:
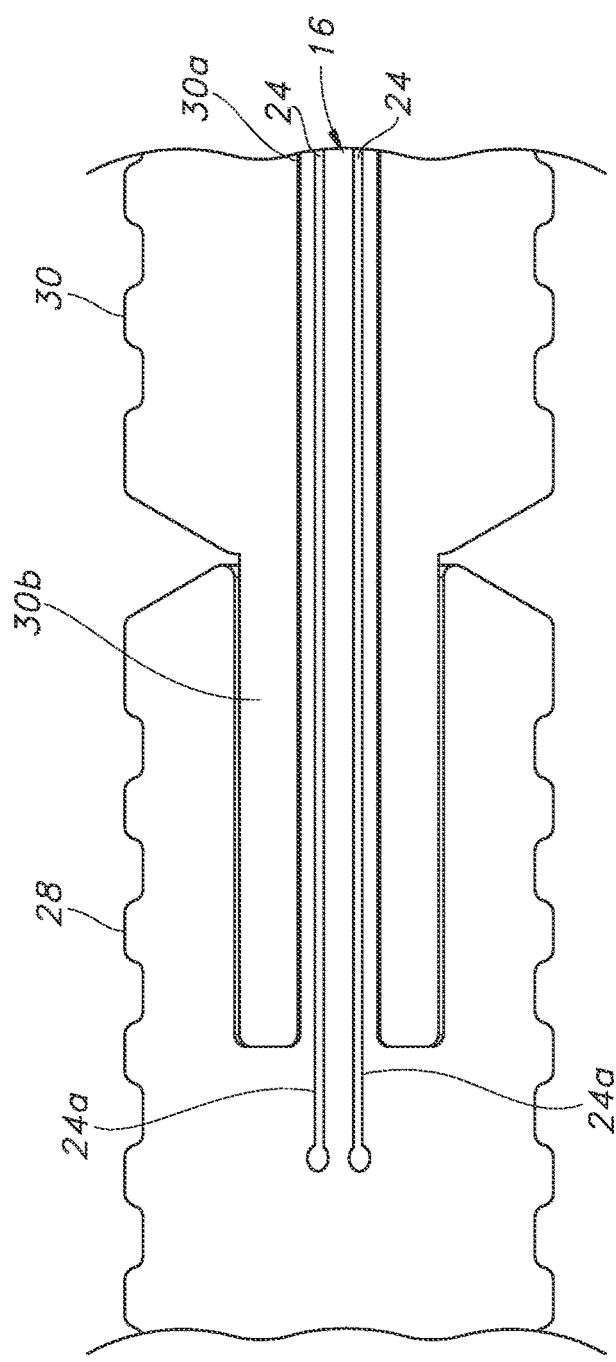
FIG. 5A is an enlarged, cutaway side view of the proximal end of the catheter.

Referring to FIGS. 5A and 8, a proximal end 24a of each wire 24 may extend from the proximal end 12a of the shaft 12 for manual grasping and pulling. Optionally, each proximal end 24a may be connected to a pull 28 associated with and proximal to a hub 30 at the proximal end 12a of the catheter 10, such that all wires 24 can be pulled simultaneously. The proximal ends 24a of the wires 24 may be embedded in or otherwise captured by the material of the pull 28, as indicated in FIG. 5A.

Figure 5B:
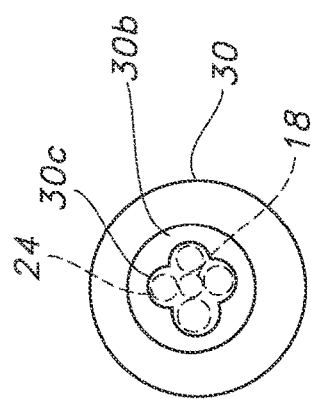
FIG. 5B is an end view of a portion of the catheter.

As shown in FIG. 6, the shaft 12 may include a lumen 32 for each wire 24, which also extends through a lumen 30a in the hub 30. As indicated, the guidewire 18 may pass through both the pull 28 and hub 30 (via lumens 28a, 30a), which as shown in FIG. 5 may be designed to nest together in the nominal configuration (note reduced diameter portion 30b of hub 30 nested in a bore 28b of pull 28). Furthermore, the open end of the bore 30c in the reduced diameter portion 30b may have cutouts, as shown in FIG. 5B, to prevent relative rotation of the wires 24.

To allow for radial expansion of the balloon 20 in the illustrated embodiment, the shaft 12 may be provided with one or more inflatation lumens 36. As shown in FIGS. 6 and 7, the inflation lumens 36 may communicate with an interior compartment of the balloon 20 to introduce an inflation fluid supplied to a proximal end, such as via a port 38. This port 38 may be connected to hub 30 and adapted for releasably connecting to a source of pressurized fluid (e.g., an inflator or pump for introducing saline or the like).

Proximal and distal radiopaque markers 40a, 40b may be provided on the shaft 12 adjacent the distal and proximal passages 12c, 26a for each of the one or more cutters 22 present, as indicated in FIG. 3 with the cutters recessed in the distal receivers. These markers 40a, 40b may take the form of bands, and indicate the position of the cutters 22 in the recessed or non-deployed condition. The resulting enhanced locatability under fluoroscopy facilitates proper positioning of the catheter 10 in the vasculature for purposes of slicing or scoring a lesion, and allows the clinician to understand the non-deployed positions of the cutters 22 from outside of the vasculature. The cutters 22 may also be formed of a radio-paque material (e.g., stainless steel or a radiopaque polymer material) so that their location along the expandable portion is known during the procedure.

With reference to FIGS. 9 and 10-12, actuation of the one or more cutters 22 is illustrated. Once the catheter 10 is located at a desired treatment location in the vasculature, with the assistance of a pre-placed guidewire 18, the expandable portion, such as balloon 20, is expanded. This may be achieved by supplying inflation fluid via port 38 and inflation lumens 36 to the interior compartment of the balloon 20, essentially as is done in conventional balloon angioplasty.

The pull 28 may then be moved in the proximal direction, as shown in FIGS. 8 and 9 (note alternate position of pull 28') and indicated by action arrow A. This simultaneously translates the connected wires 24 proximally. Consequently, distal ends 24b of the wires 24 are moved proximally in sheath 26 in FIG. 11, which ends should be sufficiently long in the longitudinal direction to avoid being withdrawn from the receiver when the cutters 22 are in the non-deployed proximal position.

This movement of the wires 24 in turn results in the attached cutters 22 alighting from the corresponding passages 12c and travelling along the outer surface of the balloon 20 in the expanded condition in a proximal direction (note arrow P), performing a cutting or slicing function of an adjacent or surrounding lesion during the guided linear movement. As can be appreciated, the cutters 22 at all times are reliably guided for substantially linear movement along the longitudinal axis X by the associated wires 24, the proximal and distal ends 24a, 24b of which remain at least partially captured within the proximal shaft 12 and distal sheath 26 forming a portion thereof, which thereby serve as the receivers. This prevents the cutters 22 from moving in the circumferential direction to any significant degree during the axial movement, and advantageously ensures that the desired score line or slice is achieved.

Once the desired score line or slice is created by passing the cutter(s) 22 through the lesion linearly, the proximal movement may be continued until the cutter(s) enter the proximal passages 12c and achieve a non-deployed position. In this fully retracted position, the cutters 22 are shielded by the shaft 28 and thus cannot perform a scoring or slicing function. This is true even as the catheter 10 is withdrawn from the vasculature.

At that point, the expandable portion of the catheter 10, or balloon, may be deflated. If repeating of the cutting is desired, the cutters 22 may be advanced distally by pushing on the pull 28 until entry into the distal passages 26a is achieved. The above-described process may then be repeated for the same lesion as many times as desired (perhaps with bodily rotation of the catheter 10 to create a rotated score line during the next pass). Alternatively, the catheter 10 may be moved to another position in the same vessel or elsewhere in the vasculature for further scoring or slicing, or withdrawn.

As an alternative mode of operation, once the catheter 10 is positioned appropriately for treating a treatment area, the cutter(s) 22 may be partially deployed to a location along the expandable portion in an expanded condition. The proximal end 12a of the catheter 10 may then be pulled proximally to cause the cutter(s) 22 to pass along the lesion and create the score or slice. The expandable portion may then be relaxed, the cutter(s) 22 returned to the receiver(s) (passages 26a) at the distal end, and the process may be repeated. Alternatively, the cutter(s) may be drawn into the proximal receivers (passages 12c) and the catheter withdrawn.

Referring now to FIGS. 12-19, and alternate embodiment of the catheter 100 is illustrated. This catheter 100 includes reciprocal cutters 122a, 122b associated with a single carrier, which again may take the form of a wire 124. The wire 124 includes a forward length 124a and a return length 124b, thus forming a loop 124c distal of the expandable portion, or balloon 120, at the distal end 112b of shaft 112. The loop 124c is normally covered by the receiver, such as sheath 126, which may include passages 126c for receiving the wire lengths 124a, 124b and lumens 132 for them and the loop 124c at the distal end 112b, as indicated in FIG. 16. As can be appreciated, since the full length of the distal end of the wire 124 does not extend along the catheter 100, as in the first embodiment, the sheath 126 may be much shorter in the longitudinal direction, as shown in FIG. 12.

The wire lengths 124a, 124b traverse proximally along the expandable portion and into proximal passages 112c associated with the shaft 112, ultimately alighting from the proximal end 112a of the shaft 112, as indicated in FIG. 15 (and the shaft 112 is shown in a truncated form for purposes of illustration with guidewire 118 exposed). In the non-deployed position, a first distal cutter 122a connected to wire length 124a is located within the distal receiver formed by sheath 126, and a second, proximal cutter 122b connected to wire length 124b is located within the proximal receiver formed by shaft 112. Radiopaque markers 140a, 140b may be provided adjacent to the passages 112c, 126a, as with the first embodiment.

With reference to FIGS. 17, 18, and 19, actuation of the reciprocal cutters 122a, 122b in opposite directions to provide concurrent scoring or slicing functionality is illustrated. Once the catheter 110 is located at a desired treatment location via guidewire 118, the expandable portion, such as balloon 120, is expanded, such as by supplying inflation fluid via port 138 and inflation lumens 136 to the interior compartment of the balloon 120, essentially as is done in conventional balloon angioplasty.

The wire length 124a may then be moved in the proximal direction, as indicated by action arrow P in FIG. 18. This translates the wire length 124a proximally, and as a result of the loop 124c, translates the wire length 124b distally (action arrow D). This causes the attached cutters 122a, 122b to alight from the opening of passages 112c, 126a and travel along the outer surface of the balloon 120 in the expanded condition in opposite directions, performing a cutting or slicing function of an adjacent or surrounding lesion (essentially, "flossing"). The proximal movement may be continued until the cutters 122a, 122b enter the proximal opening of passage 112c and distal opening of passage 126a, respectively, to achieve a non-deployed or retracted condition, as indicated in FIG. 20.

Before or after that step, it is also possible to reverse the position of cutters 122a, 122b by pulling on the wire length 124b, which causes the cutter 122a to move distally and the cutter 122b to move proximally, which may thus again slice or score the lesion. As with the first embodiment, the catheter 100 may be rotated before the reciprocal movement is achieved, such that each forward or return pass of the cutters 122a, 122b creates a circumferentially spaced score or cut in the lesion. After making one or more passes in a reciprocal fashion, the catheter 100 may be moved to another position for further scoring or slicing of a different lesion, or withdrawn.

While the use of a single wire 124 with lengths 124a, 124b forming a loop 124c is described above, it can be understood from FIGS. 13-16 that the arrangement may be repeated, such that a second looped wire 124 extends along catheter 100 for providing the same functionality using proximal and distal cutters (not shown). The second wire 124 may operate in concurrently with the first wire 124, or the two may be operated consecutively.

It can be understood that the expandable portion may take different forms. For example, as shown in FIG. 20, the expandable portion may comprise a frame 50, which may be comprised of wires 52 formed of a shape memory material, such as Nitinol. When expansion is desired, the wires 52 may be caused to assume an expanded condition (such as by way of a temperature change in the case of Nitinol), and thus provide the desired guidance for the cutter(s) 22 traversing the catheter 10 when the corresponding wire is actuated. Expandable members other than balloons 20 inflatable as a result of the introduction of external fluid may also be used, such as those made of materials that swell or expand when energized.

While the processes for actively cutting or slicing a lesion using the catheter 10 described above may be manually completed, automation is possible. For example, as indicated in FIG. 17, the proximal the wire(s) 24 may also be associated with an actuator 60, such as for example a linear actuator, which may be controlled by a controller 70 in connection with the expansion of the expandable portion (e.g., inflation of balloon 20 by an automated inflator 80).

The same approach may also be taken with the pull 28 of the first embodiment, or it could be omitted by connecting the proximal ends of the wires 24 directly to the actuator.

While the expandable portion is shown in the above embodiments as being laterally symmetrical relative to the catheter 10 (and shaft 12 in particular), it is also possible to provide it in an asymmetrical or offset fashion relative to a longitudinal axis X. Thus, as shown in FIGS. 21-23, a further embodiment of the catheter 200 may include an offset expandable portion, which is shown as an inflatable balloon 220, but may also comprise a cage as shown in FIG. 20. A carrier, such as wire 224, may include at least one cutter 222, which may be located in a distal receiver, such as formed by a passage 226a within a distal sheath 226. A proximal receiver 212c may also be provided in the shaft 212 for receiving a proximal portion of the wire 224 and the cutter 222 at a proximal end of the expandable portion.

Thus, as can be understood from FIGS. 21 and 22, the catheter 200 may be positioned at an area for treatment, and the balloon 220 inflated via a lumen in shaft 212 (not shown; note inflated condition indicated as balloon 220', indicating that it expands a greater distance in the radial direction along one side of the catheter as compared to the other in view of the offset positioning). As can be appreciated, the contact with the wall of the vessel (not shown) forces the opposite side of the catheter 200 into proximity with the area for treatment (e.g., lesion), at which point the cutter 222 may be pulled proximally (arrow P) using the wire 224 (which may extend from the proximal end of the catheter shaft 212), and alight from the distal passage 226a to score or slice the lesion (compare distal position of cutter 222 with proximal position of cutter 222' in FIG. 22). The cutter 222 may be drawn along the shaft 212, and may be moved along a guide 212d formed therein to be urged radially into a position for engaging the lesion. Ultimately, the cutter 222 may enter the proximal receiver, such as passage 212c in the shaft 212. The expandable portion or balloon 220 may then be partially or fully deflated, and the cutter 222 returned to the distal position, and the process repeated at the same or a different location.

In any of the foregoing embodiments, the cutters 22, 122a, 112b, 222 used may be provided with a blade having a thin, razor edge of various shapes (flat, convex, chiseled, single bevel, double bevel, etc.) to provide a precision cut. The blade edges may also be serrated (single or double), scalloped, chamfered, wavy, or take other shapes or forms, depending on the particular use. Each cutter 22 may also be provided with more than one cutting element or blade.

In summary, a catheter 10 for scoring or slicing a lesion in a vessel is provided. An associated catheter shaft 12 includes an expandable portion, such as a balloon 20, a wire frame 50, or the like, and a cutter 22 connected to a carrier, such as wire 24. The cutter 22 is movable from a non-deployed position in a distal receiver (passage 26a) created by a sheath 26 forming part of the shaft 12, along the balloon 20 when expanded, guided in a linear direction to provide a scoring or slicing function, and to a proximal non-deployed position in a proximal receiver (passage 12c). In another embodiment, a catheter 100 includes a carrier or wire 124 with two generally parallel lengths 124a, 124b that include a loop 124c. Each length 124a, 124b of the wire 124 is associated with a cutter 122a, 122b. Actuation of the wire 124 causes the wire lengths and cutters to move in a reciprocal manner along the expandable portion of the catheter 10. Still a further embodiment of the catheter 200 includes an offset or asymmetrical expandable portion, which urges a cutter 222 associated with a carrier or wire 224 into engagement with an adjacent lesion.

The disclosure may be considered to relate to the following items:

1. A catheter for scoring and/or slicing a lesion in a vessel, comprising:
   a catheter shaft including a first receiver adjacent a distal end of an expandable portion of the catheter shaft; and
   a first carrier positioned at least partially within the first receiver and moveable axially to deploy a first cutter along the expandable portion for cutting and/or scoring the lesion. The catheter or first carrier may include the first cutter, which may be in the form of an upstanding blade connected to the carrier proximal of a distal end thereof.
2. The catheter of item 1, further including a first radiopaque marker distal of the expandable portion for marking a distal non-deployed position of the first cutter.
3. The catheter of item 1 or item 2, further including a second receiver proximal of the expandable portion for receiving the first cutter in a proximal non-deployed position.
4. The catheter of any of items 1 to 3, further including a second radiopaque marker proximal of the expandable portion for marking a non-deployed proximal position of the first cutter.
5. The catheter of any of items 1 to 4, wherein the first carrier includes a loop distal of the expandable portion, and a second cutter proximal to the expandable portion for moving distally along the expandable portion when the first cutter is moved to a deployed position.
6. The catheter of item 5, further including a second receiver proximal of the expandable portion for receiving the second cutter in a non-deployed proximal position.
7. The catheter of item 1, further including a second carrier at least partially received by the first receiver, the second carrier moveable axially along the catheter shaft to deploy a second cutter attached to the second carrier along the expandable portion for cutting or scoring the lesion.
8. The catheter of item 7, further including a second receiver proximal of the expandable portion for receiving the first cutter in a proximal non-deployed position.
9. The catheter of item 7 or 8, further including a pull at a proximal end of the catheter shaft connected to the first carrier and the second carrier.
10. The catheter of item 1, further including a plurality of second carriers at least partially within the first receiver, each of the plurality of second carriers moveable axially along the catheter shaft to deploy a second cutter attached to each of the second carriers along the expandable portion for cutting or scoring the lesion.
11. The catheter of item 10, further including a second receiver proximal of the expandable portion for receiving each of the second cutters in a proximal non-deployed position.
12. The catheter of item 10 or 11, further including a pull at a proximal end of the catheter shaft connected to the first carrier and the plurality of second carriers.
13. The catheter of any of the preceding items, wherein the expandable portion comprises an inflatable balloon supported by the shaft, the shaft further including an inflation lumen for supplying fluid to the inflatable balloon.

14. The catheter of any of the preceding items, wherein the expandable portion comprises an expandable frame.

14a. The catheter of any of the preceding items, wherein the expandable portion is offset from a longitudinal axis of the catheter.

15. The catheter of any of the preceding items, wherein the first receiver comprises a sheath connected to the catheter shaft for receiving a portion of the first carrier including the first cutter.

16. The catheter of item 12, wherein the catheter shaft and sheath each include a guidewire lumen.

17. The catheter of any of the preceding items, wherein the first carrier comprises a wire.

18. A catheter comprising:
   a catheter shaft having an expandable portion; and
   a first carrier extending along the expandable portion, the first carrier including a first cutter adjacent a proximal end of the expandable portion and a second cutter adjacent to a distal end of the expandable portion, the first carrier adapted for moving the first cutter along the expandable portion toward the distal end while moving the second cutter along the expandable portion toward the proximal end.

19. The catheter of item 18, wherein the carrier comprises a wire having a loop.

20. The catheter of item 19, wherein the loop is distal of the expandable portion.

21. The catheter of item 18, 19 or 20, further including a first receiver for receiving the first cutter at a proximal end of the expandable portion and a second receiver for receiving the second cutter at a distal end of the expandable portion.

22. The catheter of any of items 18 to 21, further including a first radiopaque marker proximal of the expandable portion for marking a non-deployed proximal position of the first cutter and a second radiopaque marker distal of the expandable portion for making a non-deployed distal portion of the second cutter.

22a. The catheter of any of items 21-22, wherein the expandable portion is offset from a longitudinal axis of the catheter.

The catheter of items 18 to 23 can be characterized by the features of items 2 to 21.

23. A catheter for scoring or slicing a lesion in a vessel, comprising:
   a catheter shaft including a first receiver at a distal end of an expandable portion of the catheter shaft; and
   a first cutter at least partially within the first receiver and moveable axially along the catheter shaft to a deployed position along the expandable portion for cutting or scoring the lesion.

24. The catheter of item 23, further including a carrier connected to the first cutter.

25. The catheter of item 24, wherein the carrier comprises a wire having a first portion received within a second receiver proximal of the expandable portion of the catheter shaft and a second portion received within the first receiver.

26. The catheter of item 24, wherein the carrier comprises a wire having a loop forming a first length attached to the first cutter and a second length attached to a second cutter.

27. The catheter of any of items 23 to 26, wherein the catheter shaft includes a second receiver proximal of the expandable portion for receiving the second cutter in a non-deployed condition.

27a. A catheter for scoring or slicing a lesion in a vessel, comprising:
   a catheter shaft having a longitudinal axis and an offset expandable portion;
   a first cutter; and
   a carrier positioned at least partially within the first receiver and moveable axially to deploy the first cutter along the expandable portion for cutting or scoring the lesion.

28. A method of scoring or slicing, comprising:
   providing a catheter shaft, including an expandable portion and a carrier including a first cutter;
   while the expandable portion is expanded, moving the carrier axially along a longitudinal axis of the catheter shaft between a first position wherein the first cutter does not perform a cutting and/or scoring function and a second position wherein the first cutter performs a cutting and/or scoring function.

29. The method of item 28, wherein the moving step comprises pulling the carrier connected to the first cutter.

30. The method of item 28 or 29, wherein the carrier comprises a wire, and the step of moving the carrier axially comprises pulling a first portion of the wire proximally while a second portion of the wire including a second cutter is moved distally.

31. The method of items 28 or item 29, wherein the catheter includes a plurality of carriers, each including at least one cutter, and the moving step comprises moving each wire simultaneously.

32. The method of any of items 28 to 31, further including the step of moving the catheter shaft proximally with the first cutter in the second position.

33. A method of scoring or slicing a lesion, comprising:
   slicing or scoring the lesion by moving a plurality of cutters in a reciprocal manner along an expanded portion of a catheter.

34. The method of item 33, wherein the plurality of cutters are connected to a wire, and the step of slicing or scoring the lesion comprises pulling a first portion of the wire proximally while a second portion of the wire including a second cutter moves distally.

35. The method of item 33 or 34, further including the step of moving the catheter proximally with the cutters is a deployed position.

Each of the following terms written in singular grammatical form: "a", "an", and the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of." Each of the phrases "consisting of" and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The invention claimed is:

1. A catheter for scoring or slicing a lesion in a vessel, comprising:
   a catheter shaft including a first receiver adjacent a distal end of an expandable portion of the catheter shaft;
   a first blade; and
   a carrier attached to the first blade, the carrier having a portion distal of the first blade positioned at least partially within the first receiver and moveable axially to deploy the first blade along the expandable portion in an expanded condition for scoring or slicing the lesion.

2. The catheter of claim 1, further including a first radiopaque marker distal of the expandable portion for marking a distal non-deployed position of the first blade.

3. The catheter of claim 1, further including a second receiver proximal of the expandable portion for receiving the first blade in a proximal non-deployed position.

4. The catheter of claim 3, further including a second radiopaque marker proximal of the expandable portion for marking a non-deployed proximal position of the first blade.

5. The catheter of claim 1, further including a second carrier at least partially covered by the first receiver, the second carrier moveable axially along the catheter shaft to deploy a second blade attached to the second carrier along the expandable portion for cutting or scoring the lesion.

6. The catheter of claim 5, further including a second receiver proximal of the expandable portion for receiving the first blade in a proximal non-deployed position.

7. The catheter of claim 5, further including a pull at a proximal end of the catheter shaft connected to the first carrier and the second carrier.

8. The catheter of claim 1, further including a plurality of second carriers at least partially within the first receiver, each of the plurality of second carriers having a second blade attached thereto and moveable axially along the catheter shaft along the expandable portion to deploy the second blades for cutting or scoring the lesion.

9. The catheter of claim 8, further including a second receiver proximal of the expandable portion for receiving each of the second blades in a proximal non-deployed position.

10. The catheter of claim 9, further including a pull at a proximal end of the catheter shaft connected to the first carrier and the plurality of second carriers.

11. The catheter of claim 1, wherein the expandable portion comprises an inflatable balloon supported by the shaft, the shaft further including an inflation lumen for supplying fluid to the inflatable balloon.

12. The catheter of claim 1, wherein the first blade comprises an upstanding blade connected to a base, and the first carrier comprises a wire connected to the base.

13. The catheter of claim 1, wherein the expandable portion is offset from a longitudinal axis of the catheter.

14. The catheter of claim 1, wherein the first receiver comprises a sheath connected to the catheter shaft for receiving a portion of the first carrier including the first blade.

15. The catheter of claim 14, wherein the catheter shaft and sheath each include a guidewire lumen.

16. The catheter of claim 1, wherein the first carrier comprises a wire.

17. A catheter comprising:
   a catheter shaft having an expandable portion; and
   a first wire extending along the expandable portion, the first wire including a first blade adjacent a proximal end of the expandable portion and a second blade adjacent to a distal end of the expandable portion, the first wire adapted for moving the first blade along the expandable portion toward the distal end while moving the second blade along the expandable portion toward the proximal end.

18. The catheter of claim 17, wherein the first wire comprises a loop.

19. The catheter of claim 18, wherein the loop is distal of the expandable portion.

20. A catheter for scoring or slicing a lesion in a vessel, comprising:
- a catheter shaft including a first receiver at a distal end of an expandable portion of the catheter shaft; and
- a first blade at least partially within the first receiver in a non-deployed position and moveable axially along the expandable portion of the catheter shaft to a deployed position for scoring or slicing the lesion.

* * * * *